United States Patent [19]
Kent et al.

[11] Patent Number: 5,902,593
[45] Date of Patent: May 11, 1999

[54] TOPICALLY APPLIED PERSONAL LUBRICANT CONTAINING BENZALKONIUM CHLORIDE AS THE ACTIVE INGREDIENT

[76] Inventors: Frances B. Kent, 183 Moraine Rd.; Jason C. Birnholz, 440 Moraine Rd., both of Highland Park, Ill. 60035

[21] Appl. No.: 08/958,203

[22] Filed: Oct. 1, 1997

[51] Int. Cl.⁶ .................. A61K 9/00; A61K 9/06
[52] U.S. Cl. .................. 424/401; 514/944; 514/947
[58] Field of Search ............. 424/401; 514/944, 514/947

[56] References Cited

U.S. PATENT DOCUMENTS

| | | | |
|---|---|---|---|
| 4,956,355 | 9/1990 | Prendergast | 514/178 |
| 5,310,545 | 5/1994 | Eisen | 424/49 |
| 5,407,663 | 4/1995 | Eisen | 424/49 |
| 5,433,219 | 7/1995 | Spery | 128/844 |
| 5,443,840 | 8/1995 | Morancais | 424/450 |
| 5,466,463 | 11/1995 | Ford . | |
| 5,563,171 | 10/1996 | Brazzell et al. . | |
| 5,598,852 | 2/1997 | Spery | 128/844 |
| 5,603,933 | 2/1997 | Dwyer et al. | 424/185.1 |
| 5,637,293 | 6/1997 | Honda | 424/62 |
| 5,661,170 | 8/1997 | Chodosh . | |
| 5,708,023 | 1/1998 | Modak et al. . | |
| 5,723,269 | 3/1998 | Akagi et al. . | |

*Primary Examiner*—Thurman K. Page
*Assistant Examiner*—Brian K. Seidleck
*Attorney, Agent, or Firm*—Charles E. Temko

[57] ABSTRACT

A topically applied aphrodisiac dispersed in a manually applied vehicle which substantially increases tissue sensation. The principal ingredient is benzalkonium chloride in a water soluble gel which includes sorbitol, glycerin, hydroxyethylcellulose and propylene glycol.

3 Claims, No Drawings

TOPICALLY APPLIED PERSONAL LUBRICANT CONTAINING BENZALKONIUM CHLORIDE AS THE ACTIVE INGREDIENT

BACKGROUND OF THE INVENTION

This invention relates generally to the field of chemical aphrodisiacs and more particularly to a topical medicament which is applied to sensitive tissue areas to produce increased sensitivity to physical contact.

Internally taken aphrodisiacs are well-known in the art as is the resultant psychological effect of using the same. The use of such preparations, in many cases, is accompanied by some disadvantages, including time delay before taking effect, various side effects resulting from ingestion, and often, the lack of useful effect The use of benzalkonium chloride as a virucidal agent in the treatment of AIDS and related disease is known, as is the use of this compound as a spermicidal agent when incorporated into a suppository. It is also known to use this composition in aqueous, Quaternary ammonium antiseptics, and disinfectants.

SUMMARY OF THE INVENTION

Briefly stated, the invention contemplates the use of benzalkonium chloride as a skin and tissue sensitizer, particularly effective when manually applied in a gel vehicle to vaginal areas, wherein the thinly spread gel also serves as an effective lubricant. The product may be applied immediately before intercourse, and will remain effective for a substantial period of time thereafter.

We have found that the disclosed composition may also be used effectively for enhancing detection (and exclusion) of breast tumors by manual physical examination, the composition providing a slippery interface that facilitates palpitation of solid structures within a soft and pliant breast as well as providing sensory enhancement of the fingertips.

DETAILED DESCRIPTION OF THE DISCLOSED EMBODIMENT

In accordance with the invention, the disclosed embodiment is in the form of a water soluble gel. The principal effective ingredient is benzalkonium chloride in a spreadable vehicle, which may include other known ingredients to provide desirable characteristics in terms of odor, spreadability, adherence to the applied area; and chemical stability. A suitable gel may include water; sorbitol, glycerin, hydroxyethylcellulose, propylene glycol, and citric acid. Other operational ingredients may include methylchlyoroisothiosolanome, methylisothiazolinome (as preservatives), ginseng extract and fragrances. The following example is illustrative. Parts are by weight.

EXAMPLE 1

| | |
|---|---|
| Water | 87.88% |
| Sorbitol | 5.00% |
| Glycerine | 5.00% |

EXAMPLE 1-continued

| | |
|---|---|
| Hydroxyethylcellulose | 1.50% |
| Benzalkonium Chloride | 0.50% |
| Methylchloroisothiazolinone & Methylisothiazolinone | 0.06% |
| Fragrance | 0.05% |
| Propylene Glycol & Ginseng Extract | 0.01% |
| Citric Acid | q.s. |

The gel forming components are preferably first mixed in a suitable mixing device, following which the benzalkonium chloride is added. Operations may be conducted at room temperature. The resultant product is preferably packaged in a flexible tube suitable for dispensing upon the fingers of a user for direct application.

While it is difficult to quantify the degree of increased sensitivity obtain, the product has been tested, by individuals who applied a light coating of the gel to appropriate areas immediately before intercourse. Without exception, each of the users reported increased pleasure during intercourse to a substantial degree when compared to intercourse without using the product due to increased skin sensitivity. In some cases, the product was applied by coating the outer surface of a condom. The effect was observed to extend over a substantial period of time after application. No observable side effects obtained. It is to be noted that all of the ingredients in the product have been approved for medical use by the Federal Food & Drug Administration.

The composition also has further utility in the area of manual examination in the detection of breast tumors. It may be applied to the skin of the patient in the area of interest, or to the fingertips of the physician to provide a slippery interface enhancing the sensory ability in detecting relatively hard lumps within softer breast tissue, this being the result not only of increased sensitivity, but enhanced lubricity.

We wish it to be understood that we do not consider the invention to be limited to the precise details set for in the specification, for obvious modifications will occur to those skilled in the art to which the invention pertains.

We claim:

1. The method of making a topically applied aphrodisiac composition comprising the steps of:

a) providing a water soluble gel consisting essentially of water, sorbitol, glycerin, and hydroxyethylcellulose, and b) adding an active ingredient consisting solely of benzalkonium chloride in the proportion of approximately 0.50 percent by weight.

2. The composition formed in accordance with the method set forth in claim 1 in an ointment.

3. A method for stimulating skin sensitivity during sexual intercourse comprising the steps of:

a) providing an ointment in accordance with claim 2; and b) applying said ointment to genital areas as a thin coating.

* * * * *